United States Patent [19]

Sumita

[11] Patent Number: 5,137,534
[45] Date of Patent: Aug. 11, 1992

[54] METHOD FOR PRODUCING DENTAL AND MEDICAL BONE PROSTHESIS AND BONE PROSTHESIS PRODUCED THEREBY

[75] Inventor: Masaya Sumita, Tokyo, Japan

[73] Assignee: Asahi Kogaku Kogyo K.K., Tokyo, Japan

[21] Appl. No.: 691,664

[22] Filed: Apr. 25, 1991

Related U.S. Application Data

[63] Continuation of Ser. No. 295,322, Jan. 10, 1989, abandoned.

[30] Foreign Application Priority Data

Jan. 11, 1988 [JP] Japan ................................. 63-3496
Nov. 25, 1988 [JP] Japan ............................. 63-297794

[51] Int. Cl.$^5$ .......................................... A61F 2/28
[52] U.S. Cl. ................................... 623/16; 623/66; 433/201.1; 523/115
[58] Field of Search ................. 623/16, 66; 433/201.1; 523/114, 115

[56] References Cited

U.S. PATENT DOCUMENTS

| | | |
|---|---|---|
| 4,610,692 | 9/1986 | Eitenmuller et al. |
| 4,668,295 | 5/1987 | Bajpai ............................ 623/66 X |
| 4,677,140 | 6/1987 | Shiotzu ............................ 523/116 |
| 4,693,986 | 9/1982 | Vit et al. ......................... 623/16 X |

FOREIGN PATENT DOCUMENTS

| | | |
|---|---|---|
| 0166263 | 1/1986 | European Pat. Off. |
| 2008010 | 8/1971 | Fed. Rep. of Germany |
| 3424292 | 1/1985 | Fed. Rep. of Germany |
| 61-9265 | 3/1986 | Japan |
| 61-83107 | 4/1986 | Japan |
| 62-281953 | 12/1987 | Japan |
| 3-30361 | 2/1988 | Japan |
| 2142915 | 1/1985 | United Kingdom |

OTHER PUBLICATIONS

"Studies on Calcium Sulfates and Phosphates," Report of National Institute for Researches in Inorganic Materials, vol. 24, 1980.

Adv. Dent. Res., 2(1):181-186, Aug. 1988 (Chow) "Calcium Phosphate Materials: Reactor Response".

11th Annual Mtg. of the Society for Biomaterials, San Diego, CA, Apr. 25-28, 1985 (Hidaka et al) "Hydroxyapatite Gravels (Porous and Dense)", p. 112.

Adv. Dent. Res., 2(1): 164-180, Aug. 1988 (LeGaros) "Calcium Phosphate Materials in Restorative Dentistry".

Tokyo Medical and Dental Univ. School of Dentistry, Tokyo, Japan; 8th Mtg. Society of Biomaterials, Apr. 24-27, 1982 (Yomazaki) "Exp. Study of Porous Apatite as Artifial Bone".

Journal of Orthopaedic Research 3:65-77, No. 1, 1985 (Uchida et al) "Bone Ingrowth into Three Different Porous Ceramics".

School of Dentistry Tokyo Medical and Dental University, pp. 614-615, Nov. 4-6, 1987 (Ogawa et al) "Porous Hydroxy Apatite: Its Properties and Clinical Applications".

Primary Examiner—Randall L. Green
Assistant Examiner—Paul Prebilic
Attorney, Agent, or Firm—Sughrue, Mion, Zinn, Macpeak & Seas

[57] ABSTRACT

A method for producing a dental and medical bone prosthesis comprising the step of: adding an aqueous acidic solution of an organic or inorganic acid, such as phosphoric acid, citric acid, or acetic acid, to a fixable granulated bone prosthesis comprising at least one of α-tricalcium phosphate and tetracalcium phosphate; and a dental and medical bone prosthesis produced thereby.

20 Claims, 2 Drawing Sheets

METHOD FOR PRODUCING DENTAL AND MEDICAL BONE PROSTHESIS AND BONE PROSTHESIS PRODUCED THEREBY

This is a continuation of application No. 07/295,322 filed Jan. 10, 1989 now abandoned.

FIELD OF THE INVENTION

The present invention relates to an improved dental and medical bone prosthesis, and more particularly, relates to a method for fixing a fixable granulated bone prosthesis to produce a dental and medical bone prosthesis.

BACKGROUND OF THE INVENTION

Calcium phosphate compounds, in particular hydroxyapatite, have an excellent biocompatibility and their use as biomaterials in medical or dental fields has been widely investigated.

It has been widely investigated that hydroxyapatite is used as medical and dental bone prosthesis or granulated bone prosthesis because of their excellent biocompatibility and osteo-conductivity, and several products have been utilized practically.

Conventionally, two types of bone prosthesis have been used, i.e., a granulated bone prosthesis and a block-form bone prosthesis which has been molded into a desired form before use (as described, e.g., in *Transactions of the 11th Annual Meeting of the Society of Biomaterials*, page 112 (1985); J. Periodontol., vol. 56, page 63 (1985); J. Prosthet. Dent., vol. 49, page 461 (1983); Transactions of the 8th Annual Meeting of the Society of Biomaterials, page 100 (1982); J. Orthop. Res., vol. 3(1), page 65 (1985); and Abstract of Sintering 87, page 614 (1987)). The granulated bone prosthesis has been widely used because it can be filled freely in a bone defect having any shape.

However, the granulated bone prosthesis is often scattered and lost before the prosthesis accretes to regenerated bone. In order to avoid this disadvantage, i.e., to prevent the lost of the granulated prosthesis by fixing, it has been investigated to use fibrin adhesive as a fixing agent, but the use of fibrin adhesive has possibility of incurring hepatitis, aquired immune deficiency syndrome or the like infections because fibrin adhesive is made from human blood.

SUMMARY OF THE INVENTION

An object of the invention is to provide a method for fixing a fixable dental and medical granulated bone prosthesis which is excellent in adhesiveness between respective particles and not lost after filling in bone defects without any harmful influences to living bodies such as incurring infections.

Other objects and effects of the present invention will be apparent from the following description.

The present invention provides, in one aspect, a method for producing a dental and medical bone prosthesis comprising the step of: adding an aqueous acidic solution to a fixable granulated bone prosthesis comprising at least one of α-tricalcium phosphate and tetracalcium phosphate.

In another aspect, the present invention provides a dental and medical bone prosthesis produced by the step of: adding an aqueous acidic solution to a fixable granulated bone prosthesis comprising at least one of α-tricalcium phosphate and tetracalcium phosphate.

DETAILED DESCRIPTION OF THE INVENTION

Figure 1:
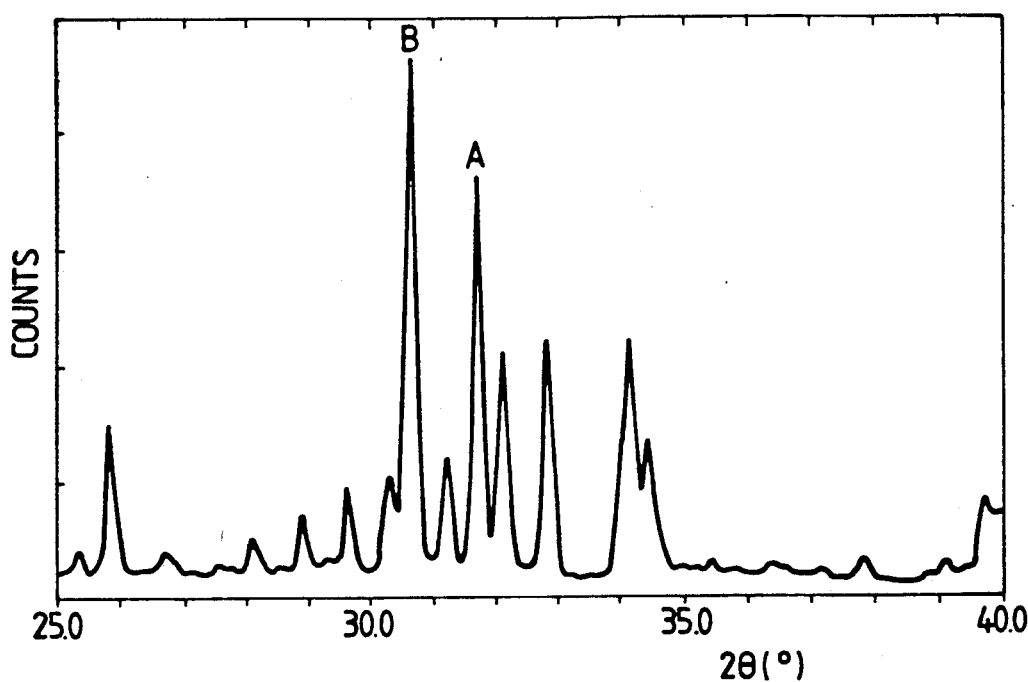
FIG. 1 is an X-ray diffraction scan of the granulated bone prosthesis obtained in Example 1.

As a result of various studies conducted in order to solve the aforementioned problems of the prior art, the present inventor has found that a granulated bone prosthesis can be fixed in bone defects without incurring any infection by using (a) a granulated bone prosthesis comprising at least one of α-tricalcium phosphate and tetracalcium phosphate, and optionally at least one of hydroxyapatite and β-tricalcium phosphate; and (b) an aqueous acidic solution. The present invention has been accomplished on the basis of this finding.

The fixable granulated bone prosthesis used in the present invention comprises at least one of α-tricalcium phosphate and tetracalcium phosphate, and may further comprise at least one of hydroxyapatite and β-tricalcium phosphate. When these calcium phosphate components are used in combination of two or more of them, the mixing ratio is not particularly limited, but the ratio of the total amount of α-tricalcium phosphate and tetracalcium phosphate to the total amount of the other components is preferably 1:3 by weight or more in view of the activity on the fixing reaction of the granulated prosthesis. These calcium phosphate components need not be completely pure and they may contain minor amounts of impurities which are generated during the synthesis.

Among the above calcium phosphate components, the following compounds and mixtures are preferably used in the present invention: (1) α-tricalcium phosphate, (2) tetracalcium phosphate, (3) a mixture of α-tricalcium phosphate and tetracalcium phosphate, (4) a mixture of α-tricalcium phosphate and hydroxyapatite, (5) a mixture of tetracalcium phosphate and hydroxyapatite, (6) a mixture of tetracalcium phosphate and β-tricalcium phosphate, and (7) a mixture of α-tricalcium phosphate and β-tricalcium phosphate.

In the present invention, calcium phosphate components containing hydroxyapatite are particularly preferably used because of excellent biocompatibility and excellent osteo-conductivity of hydroxyapatite.

α-Tricalcium phosphate (1) can be prepared by: the dry method in which calcium carbonate and calcium pyrophosphate (which is obtained by heating calcium hydrogenphosphate dihydrate at 550° C. for 2 hours) are reacted with each other at 1,200° C. for 1 hour (as described, e.g., in *Gypsum & Lime*, No. 188, page 11 (1984) and *Seitai Zairyo* (Journal of Japanese Society for Biomaterials), vol. 4, No. 3, page 51 (1986)); or the wet method in which phosphoric acid and calcium hydroxide are reacted with each other in an aqueous solution followed by calcining at from 1,120° to 1,180° C. or higher temperatures (as described, e.g., in Bioceramics no Kaihatu to Rinsho (Bioceramics-Development and Clinical Application), page 86, published by Quintessence Shuppan, Japan on Apr. 10, 1987).

Tetracalcium phosphate (2) can be prepared by the dry method in which calcium carbonate and calcium pyrophosphate are reacted with each other at 1,500° C.

(as described, e.g., in *Shika Zairyo, Kikai* (Journal of the Japanese Society for Dental Materials and Devices), vol. 5, special issue 7, page 50 (1986)).

A mixture of α-tricalcium phosphate and tetracalcium phosphate (3) can be prepared by: the thermal decomposition method in which calcium phosphate having a molar Ca/P ratio of more than 1.5 and 1.8 or less is calcined at from 1,150° to 1,450° C. under a reduced pressure, or in which hydroxyapatite obtained by the wet method is calcined at 1,500° C. for 24 hours (as described in *Transaction of Showa-62 Annual Meeting of Ceramics Society of Japan*, page 931 (May 12, 1987); or mixing α-tricalcium phosphate and tetracalcium phosphate each having been prepared separately (as described in *Shika Zairyo, Kikai* (Journal of the Japanese Society for Dental Materials and Devices), vol. 5, special issue 7, page 50 (1986)).

A mixture of α-tricalcium phosphate and hydroxyapatite (4) can be prepared by: the thermal decomposition method in which calcium phosphate having a molar Ca/P ratio of more than 1.5 and less than 1.67 is calcined at 1,000° C. or more, preferably from 1,150° to 1,450° C.; or mixing α-tricalcium phosphate and hydroxyapatite each having been prepared separately (as described in JP-A-59-182263 and JP-A-59-88351).

Hydroxyapatite can be prepared by: the dry method in which calcium carbonate and calcium pyrophosphate are reacted with each other in steam (as described, e.g., in *Bioceramics no Kaihatu to Rinsho* (Bioceramics-Development and Clinical Application), page 53, published by Quintessence Shuppan, Japan on Apr. 10, 1987); or the wet method in which phosphoric acid and calcium hydroxide are reacted with each other in an aqueous solution (as described, e.g., in *Bioceramics no Kaihatu to Rinsho* (Bioceramics-Development and Clinical Application), page 53, published by Quintessence Shuppan, Japan on Apr. 10, 1987).

A mixture of tetracalcium phosphate and hydroxyapatite (5) can be prepared by mixing tetracalcium phosphate and hydroxyapatite each having been prepared separately.

A mixture of tetracalcium phosphate and β-tricalcium phosphate (6) can be prepared by mixing tetracalcium phosphate and β-tricalcium phosphate each having been prepared separately (as described in JP-A-59-182263).

β-Tricalcium phosphate can be prepared by: the dry method in which calcium carbonate and calcium pyrophosphate are reacted with each other at 1,000° C. (as described, e.g., in *J. Catal.*, vol. 75, page 200 (1982)); or the wet method in which phosphoric acid and calcium hydroxide are reacted with each other in an aqueous solution followed by calcining at 800° C. (as described, e.g., in *Bioceramics no Kaihatu to Rinsho* (Bioceramics-Development and Clinical Application), page 86, published by Quintessence Shuppan, Japan on Apr. 10, 1987).

The methods for preparing α-tricalcium phosphate and β-tricalcium phosphate are different from each other in the calcining temperature. The formation of α-tricalcium phosphate becomes predominant relative to the formation of β-tricalcium phosphate at a temperature range of from 1,120° to 1,180° C.

A mixture of α-tricalcium phosphate and β-tricalcium phosphate (7) can be prepared by: reacting phosphoric acid and calcium hydroxide followed by calcining at a temperature at which α-tricalcium phosphate and β-tricalcium phosphate are formed as a mixture; or mixing α-tricalcium phosphate and β-tricalcium phosphate each having been prepared separately.

The preparation of a mixture of α-tricalcium phosphate and tetracalcium phosphate (3) which is particularly preferably used in the present invention will be described in more detail below.

The two compounds, i.e., α-tricalcium phosphate and tetracalcium phosphate, may be synthesized separately and thereafter mixed in appropriate proportions.

Synthesis of α-tricalcium phosphate can be made by a known dry or wet process. Tetracalcium phosphate can be prepared by a known dry process involving the reaction between calcium pyrophosphate and calcium carbonate.

A mixture of α-tricalcium phosphate and tetracalcium phosphate can be prepared by a thermal decomposition method comprising the step of calcining, at a temperature of from about 1,150° C. to 1,450° C. under reduced pressure, a calcium phosphate having a molar ratio of Ca/P of about 1.8 or less and more than 1.5 so as to produce a mixture of α-tricalcium phosphate and tetracalcium phosphate.

In this method for producing the mixture by thermal decomposition using a reduced pressure, the calcium phosphate having a molar ratio of Ca/P of more than 1.5 but not exceeding about 1.8 can be readily synthesized by a wet method. If such calcium phosphate is calcined under reduced pressure at about 1,150° C. or more, it is thermally decomposed to form α-tricalcium phosphate and tetracalcium phosphate in admixture. The resulting mixture is uniform in composition. Such calcium phosphate generally starts to be thermally decomposed at a temperature near 1,400° C. if the pressure is atmospheric. In the method described above, because the pressure is subatmospheric, the reaction of thermal decomposition is allowed to proceed at a fairly high speed even at the relatively low temperature of about 1,150° C. This is beneficial to the purpose of simplifying the manufacturing steps and reducing the production cost.

The calcium phosphate used as the starting material in the method described above can be readily synthesized by a wet process in which an aqueous solution of phosphoric acid is reacted with a suspension of calcium hydroxide by a known method. The molar ratio of Ca/P of this calcium phosphate must be more than 1.5 and about 1.8 or less, preferably from about 1.6 to 1.8. If the molar ratio of Ca/P is 1.5, the product thus-obtained does not become a mixture but α-tricalcium phosphate per se. If the molar ratio of Ca/P exceeds about 1.8, calcium oxide which is deleterious to the human body will form during calcining. The Ca/P molar ratio of the calcium phosphate used as the starting material can be adjusted by changing the proportions of calcium hydroxide and phosphoric acid which are to be reacted in the synthesis process of the calcium phosphate. By changing the Ca/P molar ratio of the starting calcium phosphate, the proportions of α-tricalcium phosphate and tetracalcium phosphate to be finally produced can be adjusted to desired values.

After synthesis by a suitable method such as a wet process, the starting calcium phosphate is preferably rendered in powder form by suitable means such as filtration, centrifugation or spray-drying. It is also preferred for the calcium phosphate to be thoroughly dried to remove as much water as possible by a suitable method such as precalcination at a temperature of about from 500° to 700° C. before it is thermally decomposed in a subsequent calcining step.

The thus prepared calcium phosphate is calcined under reduced pressure at a temperature of from about 1,150° C. to 1,450° C. If the calcining temperature is less than about 1,150° C., the intended thermal decomposition reaction will not take place to a practically acceptable extent even if the pressure is decreased.

The granulation step may be conducted either before or after the thermal decomposition of the calcium phosphate.

The reason why the calcium phosphate is calcined under reduced pressure is that the calcinating temperature can be lowered so as to simplify the manufacturing steps and to reduce the production costs, and that a product having a high activity can be attained. The reduced pressure under which the calcium phosphate is calcined is preferably about 10 Pa or less, more preferably about $10^{-2}$ Pa or less.

When the mixture of α-tricalcium phosphate and tetracalcium phosphate is prepared by calcining, at a temperature of from about 1,150° C. to 1,450° C. under reduced pressure, a calcium phosphate having a molar ratio of Ca/P of about 1.8 or less and more than 1.5, because of the uniformity of the mixture, the activity on the fixing reaction of the granulated bone prosthesis can be heightened and the fixing reaction can proceed uniformly and sufficiently and thus a bone prosthesis having a high strength can be obtained.

The preparation of a mixture of α-tricalcium phosphate and hydroxyapatite (4) which is particularly preferably used in the present invention is described in more detail below.

The two components, i.e., α-tricalcium phosphate and hydroxyapatite, may either be synthesized separately and thereafter mixed in appropriate proportions, or be produced simultaneously by calcining a specific calcium phosphate, i.e., the thermal decomposition method. In the present invention, it is preferred that these two components are produced simultaneously by thermal decomposition.

In the case where the two components are produced separately, each of them may be prepared by any known method such as a wet method and a dry method, and then mixed in appropriate proportions by any known method such as by using a mortar or a ball mill.

In the case where the two components are produced simultaneously by thermal decomposition, a mixture of α-tricalcium phosphate and hydroxyapatite used in the present invention is prepared by the step of calcining, at a temperature of about 1,000° C. or more, a calcium phosphate having a molar ratio of Ca/P of less than 1.67 and more than 1.5, preferably from 1.62 to 1.54.

The calcium phosphate used as a starting material for producing a mixture of α-tricalcium phosphate and hydroxyapatite can be prepared by reacting a phosphoric compound with a calcium compound in which the amount of the phosphoric compound is in excess of the stoichiometric amount required for producing hydroxyapatite. For example, in a known method for producing hydroxyapatite by reacting an aqueous solution of phosphoric acid and a dispersion of calcium hydroxide, an excess amount of phosphoric acid is used to obtain the objective calcium phosphate.

The molar ratio of Ca/P of the calcium phosphate must be less than 1.67 and more than 1.5 and preferably from 1.62 to 1.54. If it is 1.5, α-tricalcium phosphate per se, which is a component of the objective mixture, is produced. If it is 1.67, hydroxyapatite per se, which is a component of the objective mixture, is produced.

The molar ratio of Ca/P of the calcium phosphate can be controlled by changing the mixing ratio of calcium hydroxide and phosphoric acid. The ratio of α-tricalcium phosphate and hydroxyapatite of the mixture can be controlled by changing the molar ratio of Ca/P of the calcium phosphate.

The calcium phosphate is preferably produced by synthesizing by a wet method and then powderized by filtering, centrifuging, spray-drying, etc.

The thus prepared calcium phosphate is calcined at a temperature of about 1,000° C. or more, preferably from about 1,150° C. to 1,450° C. If the calcining temperature is less than about 1,000° C., the intended thermal decomposition reaction will not take place to a practically acceptable extent, or only β-tricalcium phosphate is formed which has substantially no activity on the fixing reaction of the granulated bone prosthesis even if the decomposition reaction takes place. If the calcining temperature is too high, the activity on fixing reaction of the granulated bone prosthesis is reduced.

The granulation step may be conducted either before or after the thermal decomposition of the calcium phosphate.

When the mixture of α-tricalcium phosphate and hydroxyapatite is prepared by calcining the calcium phosphate having a Ca/P molar ratio of more than 1.5 and less than 1.67, because of the uniformity of the mixture, the activity on the fixing reaction of the granulated bone prosthesis can be heightened and the fixing reaction can proceed uniformly and sufficiently and thus a bone prosthesis having a high strength can be obtained.

In any of the above-described methods for producing calcium phosphate compounds, the wet methods can also be conducted according, e.g., to in *Ann. Chim. (Paris)*, vol. 7, 808 and 823 (1952); *J. Res. Nat. Bur. Stand.*, vol. 72A, 773 (1986); and *Archs. Oral Biol.*, vol. 23, 329 to 336 (1978); and the dry methods can be conducted according, e.g., to *Arch. Intern. Physiol. Biochim.*, vol. 72, 337 (1964); *Chem. Abstr.*, vol. 60, 15418a (1964); and *Studii Cercetari Chim.*, vol. 13, 157 (1962).

The above mentioned calcium phosphate components can be granulated to produce a fixable granulated bone prosthesis according to the present invention. When the preparation process of the calcium phosphate components involves a calcining step, the granulating step may be conducted either before or after the calcining step.

The granulating step used in the present invention may be (a) a high speed stirring granulation method, (b) a method in which an agglomerate of powder formed by compressing is pulverized, (c) a method in which a cake of powder formed by a wet method is pulverized, and the like, but is not construed as being limited thereto.

The average particle diameter of the fixable granulated bone prosthesis of the present invention is preferably 100 μm or more, more preferably from 100 μm to 5 mm, and particularly preferably from 300 μm to 1 mm. If it is less than 100 μm, the granulated prosthesis tends to be lost in a living body because of phagocytosis of cells such as macrophage. The shape of the granulated prosthesis of the present invention is not particularly limited.

If a foaming agent (e.g., hydrogen peroxide) or a substance which disappears by calcining (e.g., polystyrene beads) is added during the preparation of the granulated prosthesis, the resulting granulated prosthesis can be made porous by calcining.

Because the respective particles of the fixable granulated bone prosthesis of the present invention can be firmly adhered by adding thereto an aqueous acidic solution, the granulated prosthesis of the present invention is advantageously used as a bone filler.

As the aqueous acidic solution used in the present invention, any aqueous acidic solution including inorganic acids such as hydrochloric acid, sulfuric acid and phosphoric acid may be used, but organic acids that have a lower toxity than that of inorganic acids are preferably used. As the organic acids, acetic acid, citric acid, malic acid, lactic acid, etc. can be used as an aqueous solution. Among the organic acids, citric acid which has a particularly low toxicity ($LD_{50}$ of oral administration for rats: 11,700 mg/kg) is most preferably used in the present invention.

The acid concentration of the aqueous acidic solution is preferably 30 wt % or more, and more preferably from 40 to 55 wt %. If the acid concentration is too low, the mechanical strength of the bone prosthesis obtained by fixing the granulated prosthesis tends to lower.

The amount ratio of the granulated prosthesis to the aqueous acidic solution is preferably from 1 to 20, and more preferably from 1 to 5, by weight.

The granulated prosthesis of the present invention can be fixed by adding the aqueous acidic solution either after or immediately before filling the granulated prosthesis in a bone defect so as to fix the respective particles of the granulated prosthesis.

The following examples are provided for the purpose of further illustration the present invention but are in no way to be taken as limiting. All parts, ratio and percents are by weight unless otherwise indicated.

EXAMPLE 1

A slurry of a calcium phosphate was obtained by a conventional method for forming hydroxyapatite in which an aqueous solution of phosphoric acid and a dispersion of calcium hydroxide were reacted with each other, provided that the amount of the phosphoric acid solution was increased to 1.06 times the stoichiometric amount required for forming hydroxyapatite.

After the calcium phosphate slurry obtained was powderized by spray drying, a slurry was again formed by adding the powder obtained to an aqueous solution of hydrogen peroxide as a foaming agent. The resulting slurry was poured in a polypropylene vessel followed by drying to form a cake of powder. The cake was pulverized and the particle diameter was adjusted to 200 to 500 μm. The granulated particles were calcined at 1,200° C. to obtain hydroxyapatite-α-tricalcium phosphate composite particles as a granulated bone prosthesis according to the present invention.

The result of X-ray diffractiometry of the granulated prosthesis is shown in FIG. 1. In FIG. 1, peak A for hydroxyapatite and peak B for α-tricalcium phosphate appeared which confirm that a mixture of hydroxyapatite and α-tricalcium phosphate was formed.

0.1 ml of a 40% aqueous solution of citric acid was added dropwise to 0.5 g of the above prepared granulated filler. After about 10 minutes from the addition of the acidic solution, respective particles of the granulated filler were strongly adhered to each other.

EXAMPLE 2

A slurry of hydroxyapatite was obtained by a conventional method for forming hydroxyapatite in which an aqueous solution of phosphoric acid and a dispersion of calcium hydroxide were reacted with each other.

After the hydroxyapatite slurry obtained was powderized by spray drying, a slurry was again formed by adding the powder obtained to an aqueous solution of hydrogen peroxide as a foaming agent. The resulting slurry was poured in a polypropylene vessel followed by drying to form a cake of powder. The cake was pulverized and the particle diameter was adjusted to 200 to 500 μm. The granulated particles were calcined at 1,200° C. under a reduced pressure of $1.3 \times 10^{-4}$ Pa for 1 hour to obtain α-tricalcium phosphate-tetracalcium phosphate composite particles as a granulated bone prosthesis according to the present invention.

Figure 2:
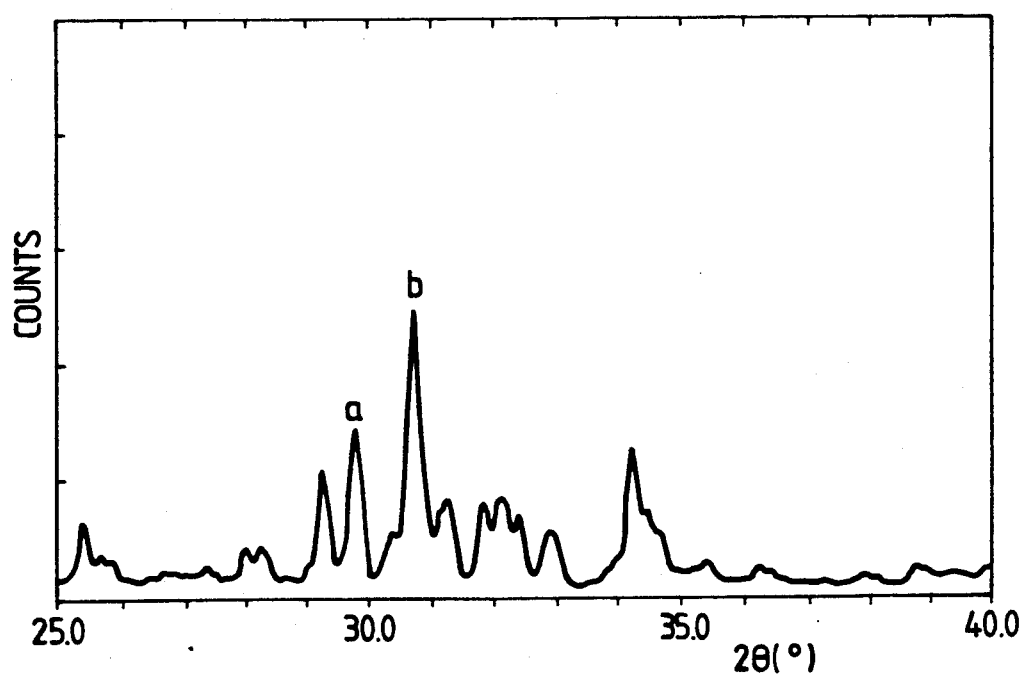
FIG. 2 is a X-ray diffraction scan of the granulated bone prosthesis obtained in Example 2.

The result of X-ray diffractiometry of the granulated prosthesis is shown in FIG. 2. In FIG. 2, peak a for tetracalcium phosphate and peak b for α-tricalcium phosphate appeared which confirm that a mixture of α-tricalcium phosphate and tetracalcium phosphate was formed.

0.1 ml of a 45% aqueous solution of citric acid was added dropwise to 0.5 g of the above prepared granulated filler. After about 10 minutes from the addition of the acidic solution, respective particles of the granulated filler were strongly adhered to each other.

EXAMPLE 3

The same procedures as in Example 2 were repeated except that a 45% aqueous solution of malic acid was used instead of the 45% aqueous solution of citric acid used in Example 2. After about 20 minutes from the addition of the acidic solution, respective particles of the granulated filler were strongly adhered to each other.

EXAMPLE 4

A slurry of tricalcium phosphate was obtained by reacting an aqueous solution of phosphoric acid and a dispersion of calcium hydroxide.

Aft the tricalcium phosphate slurry obtained was powderized by spray drying, a slurry was again formed by adding the powder obtained to an aqueous solution of hydrogen peroxide as a foaming agent. The resulting slurry was poured in a polypropylene vessel followed by drying to form a cake of powder. The cake was pulverized and the particle diameter was adjusted to 200 to 500 μm. The granulated particles were calcined at 1,200° C. in the air for 4 hours to obtain α-tricalcium phosphate particles as a granulated bone prosthesis according to the present invention.

0.1 ml of a 45% aqueous solution of citric acid was added dropwise to 0.5 g of the above prepared granulated prosthesis. After about 10 minutes from the addition of the acidic solution, respective particles of the granulated filler were strongly adhered to each other.

EXAMPLE 5

A slurry of tricalcium phosphate was obtained by reacting an aqueous solution of phosphoric acid and a dispersion of calcium hydroxide.

After the tricalcium phosphate slurry obtained was powderized by spray drying, a slurry was again formed by adding the powder obtained to an aqueous solution of hydrogen peroxide as a foaming agent. The resulting slurry was poured in a polypropylene vessel followed by drying to form a cake of powder. The cake was pulverized and the particle diameter was adjusted to 200 to 500 μm. The granulated particles were calcined at 1,180° C. in the air for 4 hour to obtain α-tricalcium phosphate-β-tricalcium phosphate composite particles as a granulated bone prosthesis according to the present invention.

Figure 3:
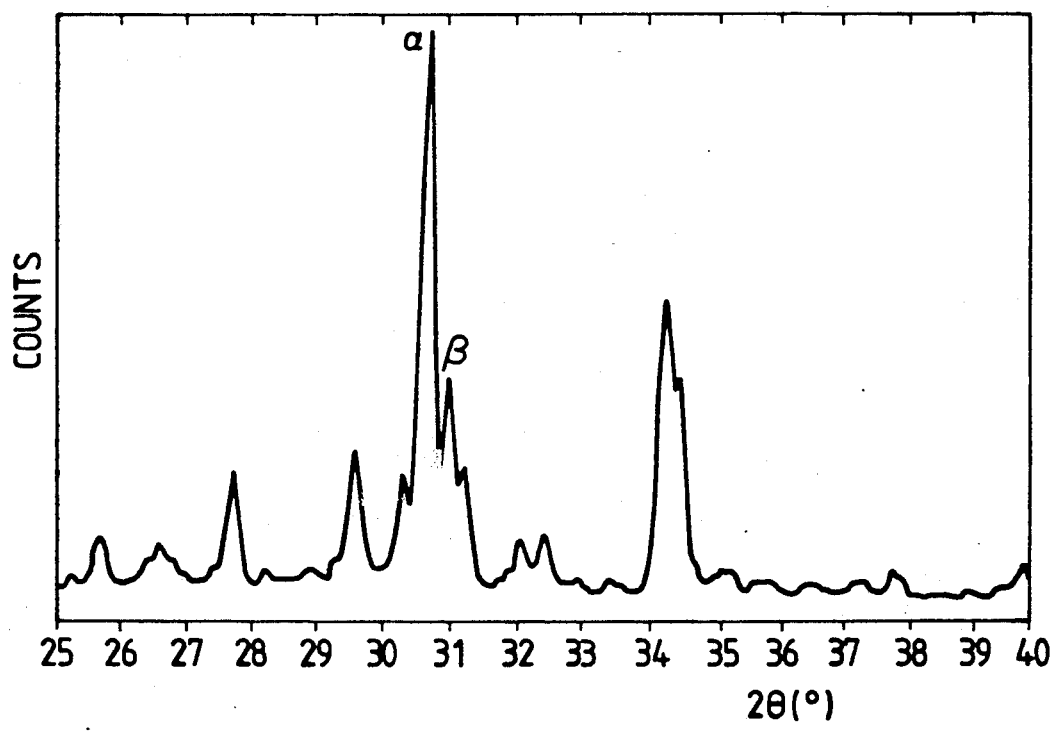
FIG. 3 is a X-ray diffraction scan of the granulated bone prosthesis obtained in Example 5.

The result of X-ray diffractiometry of the granulated prosthesis is shown in FIG. 3. In FIG. 3, peak α for α-tricalcium phosphate and peak β for β-tricalcium phosphate appeared which confirm that a mixture of α-tricalcium phosphate and β-tricalcium phosphate was formed.

0.1 ml of a 45% aqueous solution of citric acid was added dropwise to 0.5 g of the above prepared granulated filler. After about 10 minutes from the addition of the acidic solution, respective particles of the granulated filler were strongly adhered to each other.

EXAMPLE 6

Tetracalcium phosphate was obtained by reacting calcium carbonate and calcium pyrophosphate in a conventional method. After the thus-obtained tetracalcium phosphate was pulverized to form powder, it was granulated by a high speed stirring granulation method and the particle diameter was adjusted to 200 to 500 μm to obtain a granulated bone prosthesis according to the present invention.

0.1 ml of a 45% aqueous solution of citric acid was added dropwise to 0.5 g of the above prepared granulated filler. After about 8 minutes from the addition of the acidic solution, respective particles of the granulated filler were strongly adhered to each other.

According to the present invention, a granulated bone prosthesis achieves highly strong adhesiveness between the respective particles of the granulated filler by adding an aqueous acidic solution, and is not lost but maintained in a bone defect after accreting to regenerated bone. Furthermore, the granulated prosthesis of the present invention is excellent in safety because it contains no substance harmfully affecting to living bodies and has no chance of incurring infections.

While the invention has been described in detail and with reference to specific examples thereof, it will be apparent to one skilled in the art that various changes and modifications can be made therein without departing from the spirit and scope thereof.

What is claimed is:

1. A method for producing a dental and medical bone prosthesis comprising the step of: adding an aqueous acidic solution to a fixable granulated bone prosthesis comprising particles comprising at least one compound selected from the group consisting of α-tricalcium phosphate and tetracalcium phosphate, wherein said particles have a particle diameter of 200 μm or more, and wherein said aqueous acidic solution is sufficiently acidic to fuse said granules to each other by a hydration reaction.

2. A method for producing a dental and medical bone prosthesis as claimed in claim 1, wherein the ratio of the total amount of α-tricalcium phosphate and tetracalcium phosphate to the total amount of other components in said fixable granulated bone prosthesis is 1:3 by weight or more.

3. A method for producing a dental and medical bone prosthesis as claimed in claim 1, wherein said fixable granulated bone prosthesis further comprises at least one of hydroxyapatite and β-tricalcium phosphate.

4. A method for producing a dental and medical bone prosthesis as claimed in claim 1, wherein said fixable granulated bone prosthesis comprises a material selected from the group consisting of (1) α-tricalcium phosphate, (2) tetracalcium phosphate, (3) a mixture of α-tricalcium phosphate and tetracalcium phosphate, (4) a mixture of α-tricalcium phosphate and hydroxyapatite, (5) a mixture of tetracalcium phosphate and hydroxyapatite, (6) a mixture of tetracalcium phosphate and β-tricalcium phosphate, and (7) a mixture of α-tricalcium phosphate and β-tricalcium phosphate.

5. A method for producing a dental and medical bone prosthesis as claimed in claim 4, wherein said fixable granulated bone prosthesis comprises (3) a mixture of α-tricalcium phosphate and tetracalcium phosphate which is produced by the step of calcining, at a temperature of from about 1,150° C. to 1,450° C. under reduced pressure, a calcium phosphate having a molar ratio of Ca/P of about 1.8 or less and more than 1.5.

6. A method for producing a dental and medical bone prosthesis as claimed in claim 4, wherein said fixable granulated bone prosthesis comprises (4) a mixture of α-tricalcium phosphate and hydroxyapatite which is produced by the step of calcining, at a temperature of about 1,000° C. or more, a calcium phosphate having a molar ratio of Ca/P of less than 1.67 and more than 1.5.

7. A dental and medical bone prosthesis produced by a process comprising mixing granules comprising at least one compound selected from the group consisting of α-tricalcium phosphate and tetracalcium phosphate with an aqueous acidic solution, said aqueous acidic solution being sufficiently acidic to fuse said granules to each other by a hydration reaction, wherein said granules have a particle diameter of 200 μm or more.

8. A dental and medical bone prosthesis as claimed in claim 7, wherein said granulated bone prosthesis has an average particle diameter of from 200 μm to 5 mm.

9. A dental and medical bone prosthesis as claimed in claim 8, wherein said fixable granulated bone prosthesis has an average particle diameter of from 300 μm to 1 mm.

10. A method for producing a dental and medical bone prosthesis as claimed in claim 1, wherein said fixable granulated bone prosthesis is made porous upon (a) adding a foaming agent or a substance which disappears upon calcining, and (b) calcining.

11. A method for producing a dental and medical bone prosthesis as claimed in claim 1, wherein said aqueous acidic solution is an aqueous solution of an organic acid.

12. A method for producing a dental and medical bone prosthesis as claimed in claim 11, wherein said organic acid is selected from the group consisting of acetic acid, citric acid, malic acid and lactic acid.

13. A method for producing a dental and medical bone prosthesis as claimed in claim 12, wherein said organic acid is citric acid.

14. A method for producing a dental and medical bone prosthesis comprising the step of: adding an aqueous acidic solution to a fixable granulated bone prosthesis comprising particles comprising at least one compound selected from the group consisting of α-tricalcium phosphate and tetracalcium phosphate, wherein said particles have a particle diameter of 200 μm or more, and wherein said aqueous acidic solution has an acid concentration of 30 wt % or more.

15. A method for producing a dental and medical bone prosthesis as claimed in claim 14, wherein said aqueous acidic solution has an acid concentration of from 40 to 55 wt %.

16. A method for producing a dental and medical bone prosthesis as claimed in claim 1, wherein the amount ratio of said granulated bone prosthesis to said aqueous acidic solution is from 1 to 20 by weight.

17. A method for producing a dental and medical bone prosthesis as claimed in claim 16, wherein the amount ratio of said granulated bone prosthesis to said aqueous acidic solution is from 1 to 5 by weight.

18. A method for producing a dental and medical bone prosthesis as claimed in claim 1, and wherein said aqueous acidic solution is added to said fixable granulated bone prosthesis either after or immediately before said granulated bone prosthesis is used to fill a bone defect.

19. A dental and medical bone prosthesis produced by the method comprising the step of: adding an aqueous acidic solution to a fixable granulated bone prosthesis comprising at least one compound selected from the group consisting of α-tricalcium phosphate and tetracalcium phosphate, and wherein said aqueous acidic solution is sufficiently acidic to fuse said granules to each other by a hydration reaction.

20. A method of fixing a granulated bone prosthesis comprising adding an aqueous acidic solution to said granulated bone prosthesis, wherein said granulated bone prosthesis comprises particles comprising at least one compound selected from the group consisting of α-tricalcium phosphate and tetracalcium phosphate, said particles having a particle diameter of from 200 μm to 5 mm, and wherein said aqueous acidic solution is sufficiently acidic to fuse said granules to each other by a hydration reaction.

* * * * *